United States Patent [19]
Wild et al.

[11] Patent Number: 4,939,303
[45] Date of Patent: Jul. 3, 1990

[54] 3,3-DIMETHYLHEX-5-EN-2-ONE DERIVATIVES, PREPARATION AND USE THEREOF

[75] Inventors: Jochen Wild, Deidesheim; Thomas Liese-Sauer, Weinheim; Norbert Goetz, Worms; Hans Theobald, Limburgerhof; Bernd Wolf, Mutterstadt, all of Fed. Rep. of Germany

[73] Assignee: BASF Aktiengesellschaft, Ludwigshafen, Fed. Rep. of Germany

[21] Appl. No.: 301,857

[22] Filed: Jan. 26, 1989

[30] Foreign Application Priority Data

Jan. 27, 1988 [DE] Fed. Rep. of Germany ....... 3802273

[51] Int. Cl.$^5$ .............................................. C07C 49/24
[52] U.S. Cl. ........................................ 568/415; 558/52
[58] Field of Search .................... 558/52; 568/4.5, 4.6, 568/4.8

[56] References Cited

U.S. PATENT DOCUMENTS 2,957,889  10/1960  Hoaglin et al. ...................... 568/415
4,602,117   7/1986  Lantzsch ............................. 568/393

FOREIGN PATENT DOCUMENTS 95047    11/1983  European Pat. Off. ............ 508/415
3216790  11/1983  Fed. Rep. of Germany ...... 508/415
3441370   8/1985  Fed. Rep. of Germany ...... 508/415

OTHER PUBLICATIONS

Synthesis, Jul. 1981, pp. 567-570; A. B. Smith, et al.

Primary Examiner—James H. Reamer
Attorney, Agent, or Firm—Oblon, Spivak, McClelland, Maier & Neustadt

[57] ABSTRACT

3,3-Dimethylhex-5-en-2-one derivatives of the formula (I)

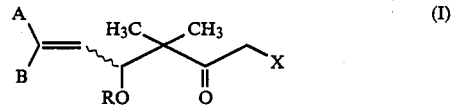

where
  A is hydrogen, halogen or $C_1$-$C_4$-haloalkyl,
  B is $C_1$-$C_4$-haloalkyl,
  X is hydrogen, or halogen and
  R is hydrogen, arylsulfonyl, alkylsulfonyl or haloalkylsulfonyl,
are used for preparing pyrethroids.

5 Claims, No Drawings

3,3-DIMETHYLHEX-5-EN-2-ONE DERIVATIVES, PREPARATION AND USE THEREOF

The present invention relates to 3,3-dimethylhex-5-en-2-one derivatives of the general formula (I)

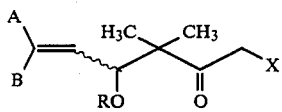

where
A is hydrogen, halogen or $C_1$-$C_4$-haloalkyl,
B is $C_1$-$C_4$-haloalkyl,
X is hydrogen or halogen and
R is hydrogen, arylsulfonyl, alkylsulfonyl or haloalkylsulfonyl, processes for preparing same and the use thereof for preparing pyrethroids or pyrethroid intermediates of the formula (V)

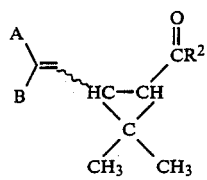

where A and B are as defined above and $R^2$ is hydroxyl, alkoxy, phenoxy or a customary pyrethroid alcohol radical.

It is known from the prior art, for example EP-A-95,047 or DE-A-3,441,370, that 3-vinyl-substituted 2,2-dimethylcyclopropanecarboxylic acids can be prepared starting from the compounds of type (A)

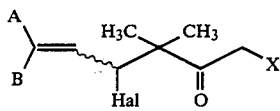

where A and B are each inter alia halogen or haloalkyl, X is hydrogen or halogen and Hal is chlorine or bromine. However, the disadvantage of this pathway is the sensitivity of compounds (A) to hydrolysis and their difficult obtainability in some instances.

β-Hydroxyketones of type (B)

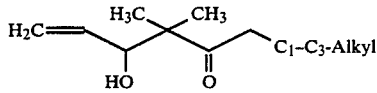

are described in Synthesis 1981, 567–570. However, their preparation by aldol condensation at −78° C. in the presence of lithium diisopropylamine is problematical, in particular for reactions on an industrial scale.

It is an object of the present invention to provide compounds which are usable to good effect as hydrolysis-insensitive starting materials for preparing pyrethroids of the formula (V) and which are obtainable in a simple and inexpensive manner.

We have found that this object is achieved with the novel 3,3-dimethylhex-5-en-2-one derivatives of the formula (I) defined at the beginning and with processes for their preparation.

The substituents in the formula (I) have specifically the following meanings:

A Hydrogen; halogen such as fluorine chlorine, bromine or iodine, in particular fluorine, chlorine or bromine;

$C_1$-$C_4$-Haloalkyl, preferably $C_1$-$C_4$-fluoro- and -chloro-haloalkyl, particularly preferably $C_1$-$C_4$-perhaloalkyl such as C Hal$_3$, $C_2$ Hal$_5$, $C_3$ Hal$_7$ or $C_4$ Hal$_9$, where each Hal is independently of the others chlorine or fluorine. Examples are trifluoromethyl, trichloromethyl, dichlorofluoromethyl, difluorochloromethyl, pentachloroethyl, pentafluoroethyl and perchlorobutyl.

B $C_1$-$C_4$-Haloalkyl, preferably $C_1$-$C_4$-fluoro- and -chloro-haloalkyl, particularly preferably $C_1$-$C_4$-perhaloalkyl such as C Hal$_3$, $C_2$ Hal$_5$, $C_3$ Hal$_7$, or $C_4$ Hal$_9$, where each Hal is independently of the others chlorine or fluorine. Examples are trifluoromethyl, trichloromethyl, dichlorofluoromethyl, difluorochloromethyl, pentachloroethyl, pentafluoroethyl and perchlorobutyl.

X Hydrogen or halogen such as fluorine, chlorine, bromine or iodine, preferably chlorine or bromine.

R Hydrogen or arylsulfonyl, alkylsulfonyl or haloalkylsulfonyl $R'$—$SO_2$—, where $R'$ is aryl, for example phenyl or phenyl substituted by inert groups, such as halogen-, cyano-, $C_1$-$C_4$-alkyl- or $C_1$-$C_4$-alkoxy-substituted phenyl, for example tolyl, p-chlorophenyl or o-bromophenyl, or $R'$ is branched or unbranched alkyl, for example $C_1$-$C_{20}$-alkyl, in particular $C_1$-$C_5$-alkyl such as methyl, ethyl, propyl, isopropyl, butyl, isobutyl, tert-butyl, pentyl or isopentyl, particularly preferably methyl or ethyl, or $R'$ is branched or unbranched $C_1$-$C_{20}$-h-aloalkyl, in particular $C_1$-$C_5$-haloalkyl, for example $C_1$-$C_5$-fluoroalkyl or -chloroalkyl, particularly preferably trifluoromethyl.

The compounds of the formula (I) according to the invention are storable, distillable and in particular, unlike compounds of structure (A), hydrolysis-stable compounds.

To prepare 3,3-dimethylhex-5-en-2-one derivatives of the formula (I) we have found the following processes:

If R and X are each hydrogen (formula (Ia) as claimed in claim (2)), it is advantageous to react a 1,3-dihalopropoxy derivative (II) with methyl isopropyl ketone (III) in the presence of a Brönstedt acid and at least one equivalent of water, based on (II), in accordance with the following reaction scheme:

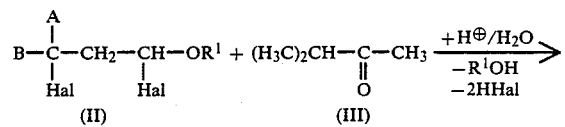

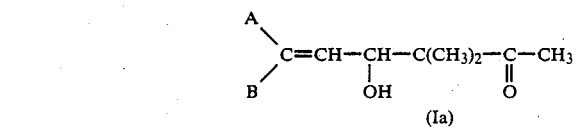

The feasibility of this process is surprising in particular in the light of the process described in DE-A-3,441,370 for preparing trihalogen-substituted 3,3-dimethylhex-5-en-2-one compounds. Instead of compounds (Ia) according to the invention one would have expected halogen-substituted products or product mixtures to be formed. The high selectivity of the reaction according to the invention together with a high yield of hydroxy ketone (Ia) was therefore unforeseeable.

The hydrolysis stability of compound (Ia) is an advantage, since this makes it possible to adjust the length of the reaction in such a way that the alpha-haloether (II) is no longer detectable in the mixture and nonetheless (I) does not decompose under the reactions conditions.

To carry out the reaction, components (II) and (III), the Brönstedt acid HA and water may be mixed in any desired order and made to react, advantageously at from 10° to 100° C., preferably at from 30° to 70° C.

To obtain an isothermal and efficiently controllable reaction, the preferred procedure, in particular with batches in the mole range or larger, comprises introducing the ketone (III), the acid HA and water initially and raising the mixture to the reaction temperature and then adding the 1,3-dihalopropoxy derivative (II).

The substituent $R^1$ in the formula (II) is unbranched or branched $C_1$-$C_{20}$-alkyl, preferably $C_1$-$C_8$-alkyl, particularly preferably $C_1$-$C_4$-alkyl, such as methyl, ethyl, propyl, isopropyl, n-butyl, isobutyl, sec-butyl or tert-butyl, aryl, preferably phenyl, 1-naphthyl, 2-naphthyl, $C_7$-$C_{20}$-aralkyl, e.g. phenylalkyl, such as benzyl, phenethyl or phenyl-n-propyl. The said radicals R1 may additionally carry substituents which are inert under the reaction conditions, for example $C_1$-$C_4$-alkyl radicals.

The compounds (II) are partly known from EP-A-31,041 and may be obtained from the corresponding vinyl ethers (VI) and the halohydrocarbons (VII) in high yields in accordance with the following reaction equation:

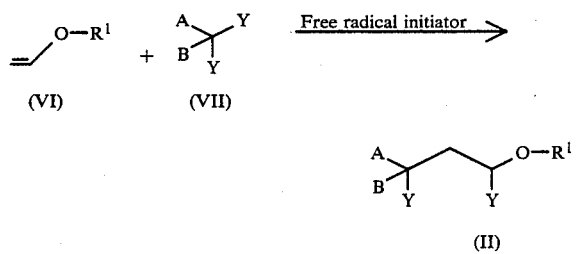

Y = chlorine or bromine by reacting in the presence of a conventional free radical initiator or by irradiation at from 0° to 120° C., preferably at from 10° to 70° C., in the presence or absence of an inert solvent. Suitable solvents are for example the halohydrocarbons (VII).

Compounds (II) may be used for the reaction with methyl isopropyl ketone (III) without purification or removal of the solvent by distillation. This is a particularly preferred embodiment of the process according to the invention, since it makes it possible to keep the handling of the alpha-haloether (II) to a minimum.

It is of course also possible to use (II) in pure form or dissolved in an inert solvent, for example an inert halohydrocarbon, preferably the halohydrocarbon used for the synthesis of (II), for the subsequent reaction.

The addition of a solvent to carry out the reaction of (II) with (III) is not absolutely necessary, but it is possible to add solvents which are inert under the reaction conditions, for example halohydrocarbons such as tetrachloromethane, methylene chloride, trifluorotrichloroethane, chloroform or pentafluorotrichloropane, or hydrocarbons such as benzene, toluene, xylene, pentane or hexane.

Suitable acidic compounds HA are inorganic acids such as hydrochloric acid, hydrobromic acid or sulfuric acid, preferably in aqueous solution, although the acids may also be used in anhydrous form.

It is also possible to use organic acids HA, for example carboxylic acids such as formic acid, acetic acid or propionic acid, dicarboxylic acids such as oxalic acid or sulfonic acids such as methanesulphonic acid, benzenesulfonic acid or p-toluenesulfonic acid. It is also possible to use acidic ion exchange resins.

The amount of acid HA is not critical, since the acid is not consumed in the course of the reaction; on the contrary, two equivalents of hydrogen halide are formed in the course of the reaction. To avoid prolonged induction periods, it is preferable to use at least from 10 mol % to 10 mole equivalents of acid HA, based on (II). Larger excesses are possible, but less economical.

The amount of water should be at least one mole, but it is preferable to use larger excesses in order to absorb the resulting hydrohalic acid in the reaction mixture. In general, amounts of from 1 to 100 moles of water, in particular from 2 to 50 moles, based on (II), may be used.

(II) and (III) are in general used in an equimolar ratio, although (III) may also be used in excess. An excess of (II) is less sensible, owing to by-product formation and the toxicity of the alpha-haloether (II). Any (III) used in excess is very simple to separate from the desired product by distillation after the reaction.

The β-hydroxy ketones (I) where R is H are convertible in a conventional manner into β-hydroxy ketones (I) where R is arylsulfonyl, alkylsulfonyl or haloalkylsulfonyl by reaction with sulfonyl halides of the formula (IV)

$$R'—SO_2—Hal \qquad (IV)$$

where R' is as defined above and Hal is halogen such as fluorine, chlorine or bromine, preferably chlorine, in the presence of a base.

The base used may be any customary agent which does not lead to the hydrolysis of the sulfonyl halide. Preference is given to using tertiary amines, in particular $C_1$-$C_8$-tri-alkylamines, or basic heteroaromatics such as pyridine or alkyl-substituted pyridines.

Examples are the following amines: trimethylamine, triethylamine, tri-n-propylamine, N,N-dimethylethylamine, N,N-dimethylisopropylamine, tri-n-butylamine, pyridine or substituted pyridines such as 2,3- or 4-methylpyridine or dimethylpyridines such as 2,6-dimethylpyridine.

The amount of base is at least one mole equivalent, based on (I), but it is preferable to use a small excess, for example from 1.05 to 1.1 moles of base per mole of (I).

It is advantageous to add catalytic amounts, for example from 0.01 to 1 mol %, of an acylation catalyst such as 4-(N,N-dimethylamino)pyridine.

The reaction may be carried out in the presence or absence of a solvent. Suitable solvents are inert organic solvents such as hydrocarbons such as benzene, toluene or petroleum ether, chlorinated hydrocarbons such as methylene chloride, chloroform or carbon tetrachloride, ethers such as dioxane or THF, or the base itself.

Compounds (I) where X is halogen are advantageously obtained by reacting compounds (I) where X is H with a halogenating agent in the presence or absence of an inert solvent. Possible halogenating agents are chlorine, bromine, sulfuryl chloride, sulfuryl bromide or N-halogen compounds such as N-bromosuccinimide (NBS) or N-chlorosuccinimide (NCS).

The reaction is customarily carried out in an inert diluent. Examples thereof are chlorohydrocarbons such as methylene chloride, chloroform, carbon tetrachloride, dichloroethane or highly chlorinated aromatics, carboxylic acids such as, for example, acetic acid, or aliphatic hydrocarbons, for example petroleum ether.

If desired, the halogenation may be carried out in the presence of a catalyst, for example a hydrohalic acid such as hydrogen chloride or hydrogen bromide, or a Lewis acid such as aluminum chloride, zinc chloride or aluminum bromide.

The reaction temperature should not exceed +70° C., the preferred temperature range being from −10° to +35° C.

In general, a maximum of up to one equivalent of halogenating agent is added; however, it is also possible to use a less than stoichiometric amount in order to prevent further halogenation of the molecule. An advantageous range is from 0.8 to 1 mole of halogenating agent.

The compounds (I) according to the invention where X is halogen and R is arylsulfonyl, alkylsulfonyl or haloalkylsulfonyl may be converted under basic conditions into 2,2-dimethylcyclopropane-1-carboxylic acid and derivatives thereof.

We found that it depends on the basic conditions used in the course of the cyclization whether the free carboxylic acid or any desired ester is obtained.

The free carboxylic acid is obtained on using alkali metal hydroxides or alkaline earth metal hydroxides such as sodium hydroxide, potassium hydroxide, lithium hydroxide, calcium hydroxide or barium hydroxide, of which potassium hydroxide and sodium hydroxide are preferred for cost reasons.

If, however, alkoxides or else phenoxides or alcohols and phenols are used in the presence of strong bases such as sodium hydride and potassium tert-butylate, the 2,2-dimethyl-1-carboxylic esters (V) of these alcohols or phenols are obtained.

Suitable alcohols are:
1. Alcohols having branched or unbranched $C_1$-$C_8$ carbon chains, for example methanol or ethanol.
2. Alcohols of the formula (B)

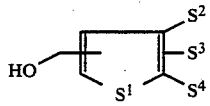

where
S¹ is a divalent oxygen radical, a divalent sulfur radical or vinylene,
S², S³ and S⁴ are each independently of the others a radical from the group consisting of hydrogen, $C_1$-$C_4$-alkyl, halogen, $C_1$-$C_4$-alkoxy, haloalkyl, haloalkoxy, $C_1$-$C_4$-alkylene, phenyl, phenoxy, benzyl and phenylthio, or two radicals at a time from the group consisting of S², S³ and S⁴ are linked together and form a divalent methylenedioxy group which is linked to two adjacent ring carbon atoms of the phenyl ring, and if the radicals S², S³ and S⁴ contain a phenyl ring, it may be substituted by from 1 to 3 substituents from the group consisting of halogen, $C_1$-$C_4$-alkoxy and $C_1$-$C_4$-alkyl.

3. Alcohols of the general formula (C)

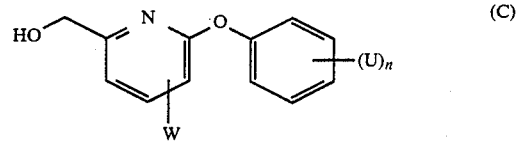

where U is hydrogen, $C_1$-$C_4$-alkyl, $C_1$-$C_4$-alkoxy, $C_1$-$C_4$-alkylthio, $C_1$-$C_4$-alkylsulfonyl, trifluoromethyl, 3,4-methylenedioxy, chlorine, fluorine or bromine, n is 1 or 2, and W is hydrogen, chlorine or fluorine.

4. Alcohols of the formula (D)

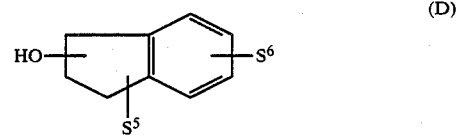

where S⁵ is hydrogen, $C_1$-$C_4$-alkyl, $C_1$-$C_4$-alkoxy, $C_1$-$C_4$-alkenyl, $C_1$-$C_4$-alkenyloxy, phenyl or benzyl and S⁶ is hydrogen, halogen, $C_1$-$C_4$-alkyl, $C_1$-$C_4$-alkoxy, $C_1$-$C_4$-alkenyl, $C_1$-$C_4$-alkenyloxy, or cyano.

5. Alcohols of the formula (E)

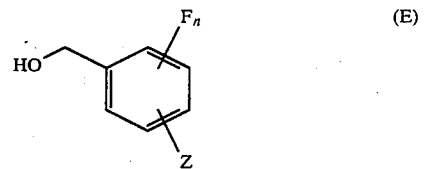

where Z is hydrogen, halogen, $C_1$-$C_4$-alkyl, $C_1$-$C_4$-alkenyl, benzyl, $C_1$-$C_4$-alkoxy $C_1$-$C_4$-alkenyloxy, $C_1$-$C_4$-alkylthio, alkylsulfonyl, alkylsulfinyl, trifluoromethyl, amino, alkoxymethyl, alkylthiomethyl, phenoxy, dialkylaminomethyl, dialkylamino, monoalkylamino, aryloxyalkyl or alkenyloxyalkyl and n is 3 or 4.

Preference, especially with regard to the synthesis of biologically active pyrethroids of the formula (IV), is given to alcohol types 2 to 5.

Typical representatives of these alcohols are for example:

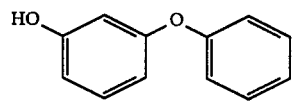

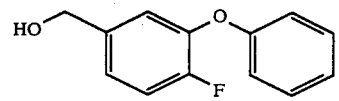

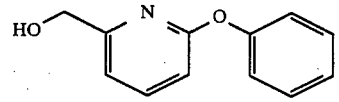

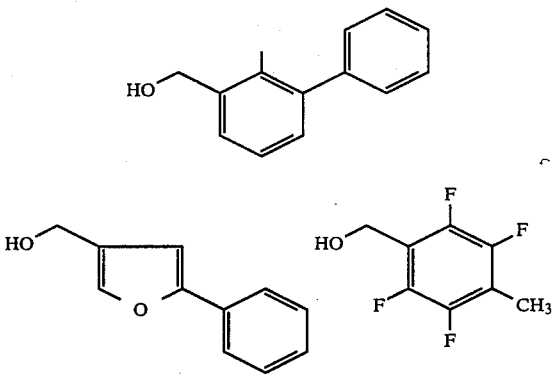

Suitable phenols are for example compounds of the structure (F)

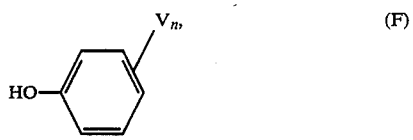

where V is any desired radical which is stable under the basic reaction conditions and n is from 0 to 5.

Preferred meanings of V are independently of one another: halogen, such as fluorine or chlorine, $C_1$–$C_4$alkyl, such as methyl, ethyl, propyl or butyl, $C_1$–$C_4$alkoxy, such as methoxy, ethoxy, propoxy or butoxy, and phenoxy, preferably p- or m-phenoxy.

Preferably, if the hydroxides are used, the reaction is carried out in water and/or an inert diluent. Suitable for this purpose are for example alcohols such as methanol, ethanol or tert-butyl, ethers such as dioxane, tetrahydrofuran (THF) or dimethoxyethane, ketones such as acetone, and dimethylformamide. However, it is also possible to use water-immiscible solvents such as methylene chloride, petroleum ether, cyclohexane, toluene or chlorobenzene in the presence or absence of a phase transfer catalyst.

If the alkoxides are used, the reaction is best carried out in the corresponding alcohols or inert solvents such as ethers, for example dioxane or THF.

Per mole of starting material of the formula (I) at least 2 equivalents of hydroxide, alkoxide or phenolate are used. An excess of base up to 3 equivalents is usually advantageous. In general, it is possible to use from 2 to 5 moles per mole of (I); a larger excess is possible, but does not give any further benefits.

The reaction temperatures may be varied within a relatively wide range, but surprisingly the reaction works even under extremely mild conditions. In general, the temperatures are within the range from 0° to 150° C., preferably from 30° to 70° C.

The reaction mixture is advantageously worked up, if the acids are to be prepared, by extraction at alkaline pH, acidification of the aqueous phase, and renewed extraction. If esters are to be prepared, the purification can take the form of a distillation. Beforehand the reaction mixture is diluted with water, brought to a neutral pH and extracted.

Under the stated conditions, the products are cis-/trans mixtures of the acids or esters (V) approximately in a ratio of from 25:75 to 35:65.

The novel 3,3-dimethylhex-5-en-2-one derivatives of the formula (I) are useful intermediates for the synthesis of crop protection agents, in particular insecticides, for example pyrethroids as described for example in the patents U.S. Pat. Nos. 4,332,815, 4,235,927 and EP-B-3,336 and the applications GB-A-2,000,764, EP-A-31,199, EP-A-200,943 and EP 145,179, which contain pyrethroids having a $CF_3$/Cl acid component.

The examples below are intended to illustrate the invention in more detail. The reported product purities were determined by gas chromatography.

A. Preparation of starting materials (II)

EXAMPLE 1

1-(n-Butoxy)-1,3,3-trichloro-4,4,4-trifluoropentane 2.06 kg of 1,1,1-trichloro-2,2,2-trifluoroethane and 9.16 g of azobisisobutyronitrile were admixed under reflux with 458 g of n-butyl vinyl ether. The mixture was refluxed for a further 6 hours, and unconverted perhaloalkane was then distilled off under reduced pressure. The residue obtained comprised 1.05 kg of product.

Yield: 80% of theory.

B. Preparation of compounds (I) according to the invention

EXAMPLE 2

6-Chloro-3,3-dimethyl-4-hydroxy-7,7,7-trifluorohept-5-en-2-one 759 g (2.6 mol) of 1-(n-butoxy)-1,3,3-trichloro-4,4,4-trifluoropropane and 681 g (7.9 mol) of methyl isopropyl ketone were admixed at 55° C. with 200 ml of concentrated hydrochloric acid in the course of 2 hours. The mixture was subsequently stirred at 55° C. for a further 30 minutes and then diluted with water, and the organic phase was separated off. Removal of unconverted methyl isopropyl ketone by distillation and subsequent distillation under reduced pressure gave 580 g of product.

Yield: 90 % of theory.
Purity: 96.7 %.

EXAMPLE 3

6-Chloro-3,3-dimethyl-4-methanesulfonyloxy-7,7,7-trifluoro-hept-5-en-2-one 733 g (3 mol) of 6-chloro-3,3-dimethyl-4-hydroxy-7,7,7-trifluoro-hept-5-en-2-one, 360 g (3.6 mol) of triethylamine and 1.5 g of 4-(N,N-dimethylamino)pyridine in 1 l of toluene were admixed at 5° C. with 378 g (3.6 mol) of methanesulfonyl chloride. The mixture was subsequently stirred at 25° C. for 3 hours, the precipitate was filtered off, and the filtrate was extracted with dilute hydrochloric acid and with saturated sodium bicarbonate solution. Drying and concentrating the organic phase gave 948 g of product. Melting point: 50°–52° C.

Yield: 97.9 % of theory.
Product purity: 98.7%.

EXAMPLE 4

1-Bromo-6-chloro-3,3-dimethyl-4-methanesulfonyloxy-7,7,7-trifluorohept-5-en-2-one 720 g (2.2 mol) of 6-chloro-3,3-dimethyl-4-methanesulfonyloxy-7,7,7-trifluorohept-5-ene-2-one in 2 l of chloroform were admixed at 20° C. with 360 g (2.2 mol) of bromine. The mixture was subsequently stirred at 20° C. for 2 hours and then concentrated. This gave 781 g of product.

Yield: 87.2% of theory.

Product purity: 82%, besides 2.3 % of 1,1-dibromo-6-chloro-3,3-dimethyl-4-methanesulfonyloxy-7,7,7-trifluorohept-5-enone and 15.7% of unconverted starting material.

The starting material may be recovered as described in Example 6 and used again in the bromination.

EXAMPLE 5

Synthesis of (Ia) without isolation of the alpha-haloether 1687 g (9 mol) of 1,1-trichloro-2,2,2-trifluoroethane and 750 g (7.5 mol) of isobutyl vinyl ether were admixed with 7 g of azobisisobutyronitrile, and the mixture was refluxed for 4 hours. According to analysis by gas chromatography, the mixture contained 66% of alpha-chloroether.

This mixture was added without further purification to a 60° C. solution consisting of 1.9 kg (22 mol) of methyl isopropyl ketone and 3 l of 50% concentrated hydrochloric acid and stirred in at 60° C. until the alpha-chloroether was no longer detectable by gas chromatography. The reacted mixture was diluted with water, and the organic phase was separated off, dried and distilled. The first cut contained unconverted trichlorotrifluoroethane and methyl isopropyl ketone and the product isobutanol. The components can be separated by fine distillation.

The main fraction consisted of 1.19 kg of product. Yield: 65% of theory, based on the vinyl ether. Product purity: 98.7%.

C Preparation of 2,2-dimethylcyclopropyl-1-carboxylic acids and esters thereof

EXAMPLE 6

3-(2-Chloro-3,3,3-trifluoroprop-1-en-1-yl)-2,2-dimethylcyclopropanecarboxylic acid A mixture obtained as described in Example 4, comprising 602 g (1.5 mol) of 1-bromo-6-chloro-3,3-dimethyl-4-methanesulfonyloxy-7,7,7-trifluorohept-5-en-2-one and 115 g (0.35 mol) of 6-chloro-3,3-dimethyl-4-methanesulfonyloxy-7,7,7-trifluorohept-5-en-2-one, was stirred at from 70° to 80° C. in 1.2 l of 10% strength aqueous sodium hydroxide solution for about 15 minutes, until a clear solution had formed.

The mixture was cooled down and extracted with methylene chloride. The extract was dried and concentrated. 105 g of 6-chloro-3,3-dimethyl-4-methanesulfonyl-7,7,7-trifluorohept-5-en-2-one were recovered for the use in a bromination as described in Example 4.

The aqueous alkali phase was acidified with hydrochloric acid, and the precipitated product was isolated by extraction with methylene chloride, giving 341 g of a crystalline mass comprising 92 g of cis-3-(Z-2-chloro-3,3,3-trifluoroprop-1-en-1-yl)-2,2-dimethylcyclopropanecarboxylic acid and 206 g of trans-3-(Z-2-chloro-3,3,3-trifluoroprop-1-en-1-yl)-2,2-dimethylcyclopropanecarboxylic acid.

Yield: 82% of theory.

EXAMPLE 7

3-Phenoxybenzyl-3-(2-chloro-3,3,3-trifluoroprop-1-en-1-yl)-2,2-dimethylcyclopropanecarboxylate

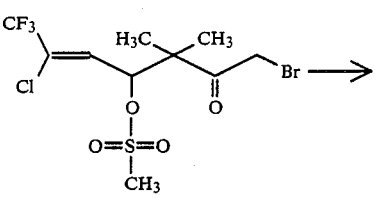

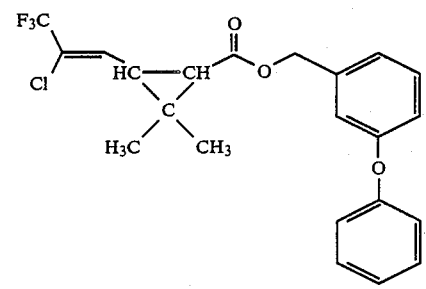

66 g (0.3 mol) of 3-phenoxybenzyl alcohol, dissolved in 50 ml of dioxane, were added dropwise at 80° C. to 7.2 g (0.3 mol) of sodium hydride in 50 ml of dioxane. The mixture was stirred at 80° C. until the gas evolution ceased. The mixture was then cooled down to 25° C., and a solution of 40.2 g (0.1 mol) of 1-bromo-6-chloro-3,3-dimethyl-4-methanesulfonyloxy-7,7,7-trifluorohept-5-en-2-one, dissolved in 50 ml of dioxane, was added dropwise. After 2 hours at room temperature the mixture was poured into water, and the aqueous mixture was extracted with methylene chloride. The excess alcohol was separated from the product by distillation under reduced pressure or by chromatography over silica gel, giving 40 g of recovered phenoxybenzyl alcohol and 24.3 g of 3'-phenoxybenzyl 3-(2-chloro-3,3,3-tfifluoroprop-1-en-1-yl)-2,2-dimethylcyclopropanecarboxylate.

Yield: 57% of theory.

EXAMPLE 8

Methyl 3-(2-chloro-3,3,3-trifluoroprop-1-en-1-yl)-2,2-dimethylcyclopropanecarboxylate 90 g of a 30% strength methanolic sodium methoxide solution were added dropwise to 40 g (0.1 mol) of 1-bromo-6-chloro-3,3-dimethyl-4-methanesulfonyloxy-7,7,7-trifluorohept-5-en-2-one in 100 ml of methanol. The mixture was heated at 50° C. until starting material was no longer detectable by gas chromatography (which took about 4 hours). The mixture was then poured into water, and the aqueous mixture was brought to pH 7 with 1N hydrochloric acid and extracted with methylene chloride. Distillation of the residue gave 18.4 g of product.

Yield: 72% of theory.

We claim:

1. A 3,3-dimethylhex-5-en-2-one derivative of formula (I):

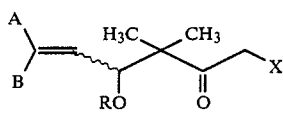 (I)

wherein A is halogen, B is $C_1$–$C_4$-haloalkyl, X is hydrogen or halogen and R is hydrogen, arylsulfonyl, alkylsulfonyl or haloalkylsulfonyl.

2. A 3,3-dimethylhex-5-en-2-one derivative of formula (I):

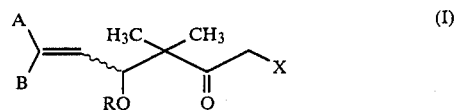 (I)

wherein A is halogen, B is $C_1$–$C_4$-perhaloalkyl, X is hydrogen or halogen and R is hydrogen, arylsulfonyl, alkylsulfonyl or haloalkylsulfonyl.

3. The 3,3-dimethylhex-5-en-2-one derivative of claim 2, wherein A is halogen and B is $CHal_3$, $C_2Hal_5$, $C_3Hal_7$ or $C_4Hal_9$, wherein each Hal is independently of the other chlorine or fluorine.

4. The 3,3-dimethylhex-5-en-2-one derivative of claim 2, wherein A is halogen and B is trifluoromethyl.

5. The 3,3-dimethylhex-5-en-2-one derivative of claim 4, wherein A is Cl, B is $CF_3$, X is hydrogen and R is hydrogen.

* * * * *